United States Patent [19]
Bell et al.

[11] Patent Number: 5,700,275
[45] Date of Patent: Dec. 23, 1997

[54] ARTICULATING ENDOSCOPIC SURGICAL INSTRUMENT

[75] Inventors: Mace H. Bell, Rowayton; Henry R. Sienkiewicz, Stamford, both of Conn.

[73] Assignee: United States Surgical Corporation, Norwalk, Conn.

[21] Appl. No.: 637,883

[22] Filed: Apr. 25, 1996

[51] Int. Cl.$^6$ .................................................. A61B 17/28
[52] U.S. Cl. ................................... 606/208; 606/206
[58] Field of Search ............................... 606/170, 205, 606/206, 207, 174, 208

[56] References Cited

U.S. PATENT DOCUMENTS

| | | |
|---|---|---|
| 723,629 | 3/1903 | Wiles . |
| 3,775,825 | 12/1973 | Wood et al. . |
| 3,964,468 | 6/1976 | Schulz . |
| 4,201,314 | 5/1980 | Samuels et al. . |
| 4,425,915 | 1/1984 | Ivanov . |
| 4,646,751 | 3/1987 | Maslanka . |
| 4,763,668 | 8/1988 | Macek et al. . |
| 4,763,669 | 8/1988 | Jaeger . |
| 4,880,015 | 11/1989 | Nierman . |
| 5,147,373 | 9/1992 | Ferzli . |
| 5,160,343 | 11/1992 | Brancel et al. . |
| 5,174,300 | 12/1992 | Bales et al. . |
| 5,209,747 | 5/1993 | Knoepfler . |
| 5,330,502 | 7/1994 | Hassler et al. . |
| 5,391,180 | 2/1995 | Tovey et al. . |
| 5,403,342 | 4/1995 | Tovey et al. ........................ 606/170 |
| 5,409,498 | 4/1995 | Braddock et al. . |
| 5,447,513 | 9/1995 | Davison et al. . |
| 5,498,256 | 3/1996 | Furnish ........................ 606/205 |
| 5,501,698 | 3/1996 | Roth et al. . |

*Primary Examiner*—Michael Buiz
*Assistant Examiner*—Kevin Truong

[57] ABSTRACT

A surgical instrument is provided having a housing defining a longitudinal axis. A handle is operably conected to the housing and defines a longitudinal axis angularly disposed relative to the longitudinal axis of the housing. A fixed support is attached to the housing and defines a longitudinal axis angularly disposed relative to the longitudinal axis of the housing. The fixed support is radially offset with respect to the handle. A body portion extends distally from the housing, and a tool assembly operably associated with a distal end portion of the body portion is remotely actuable by the handle.

29 Claims, 15 Drawing Sheets

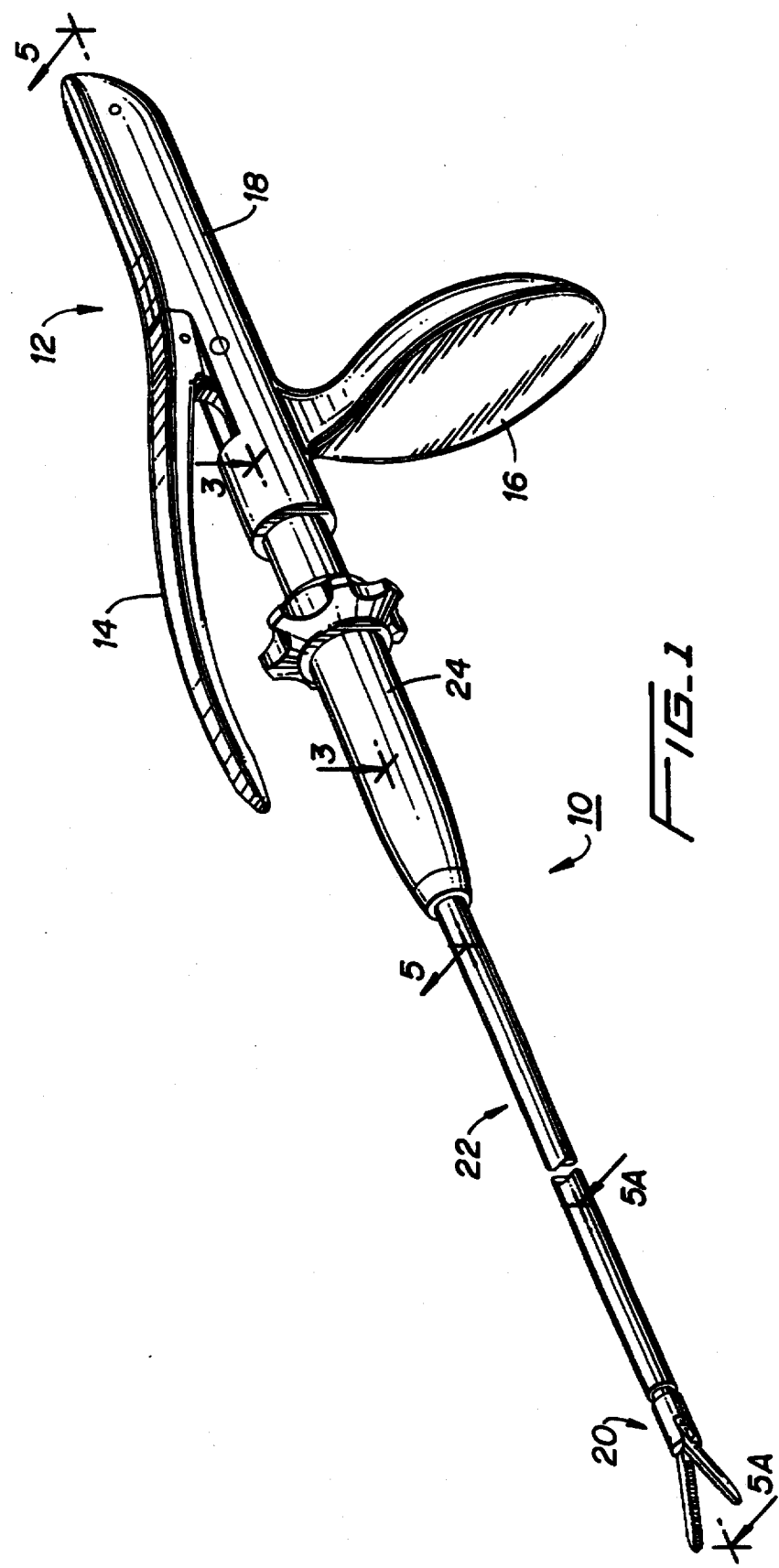

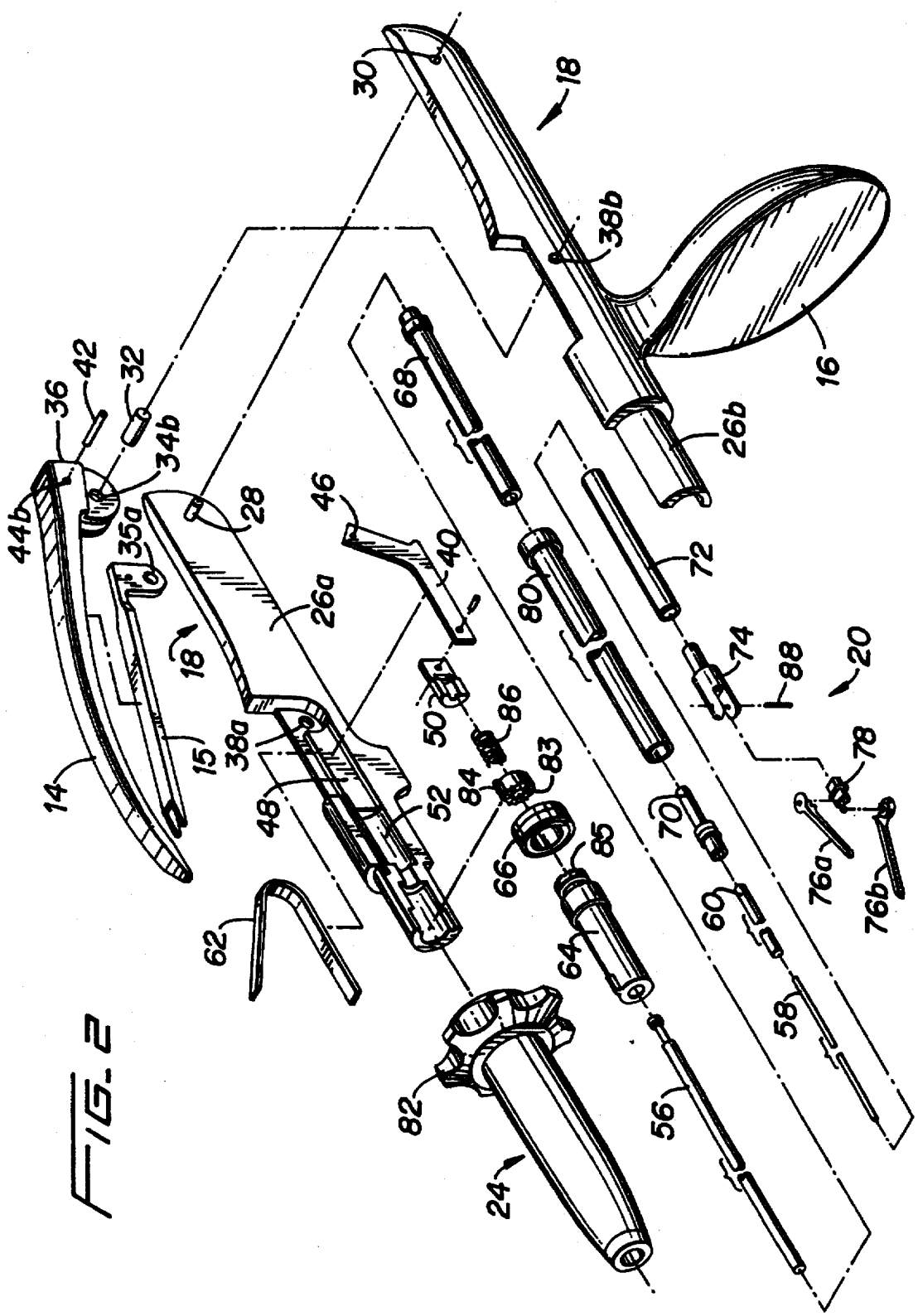

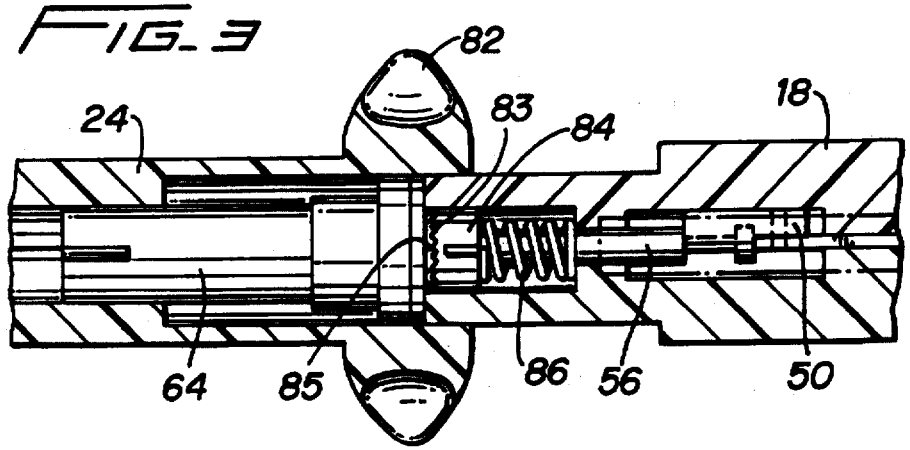
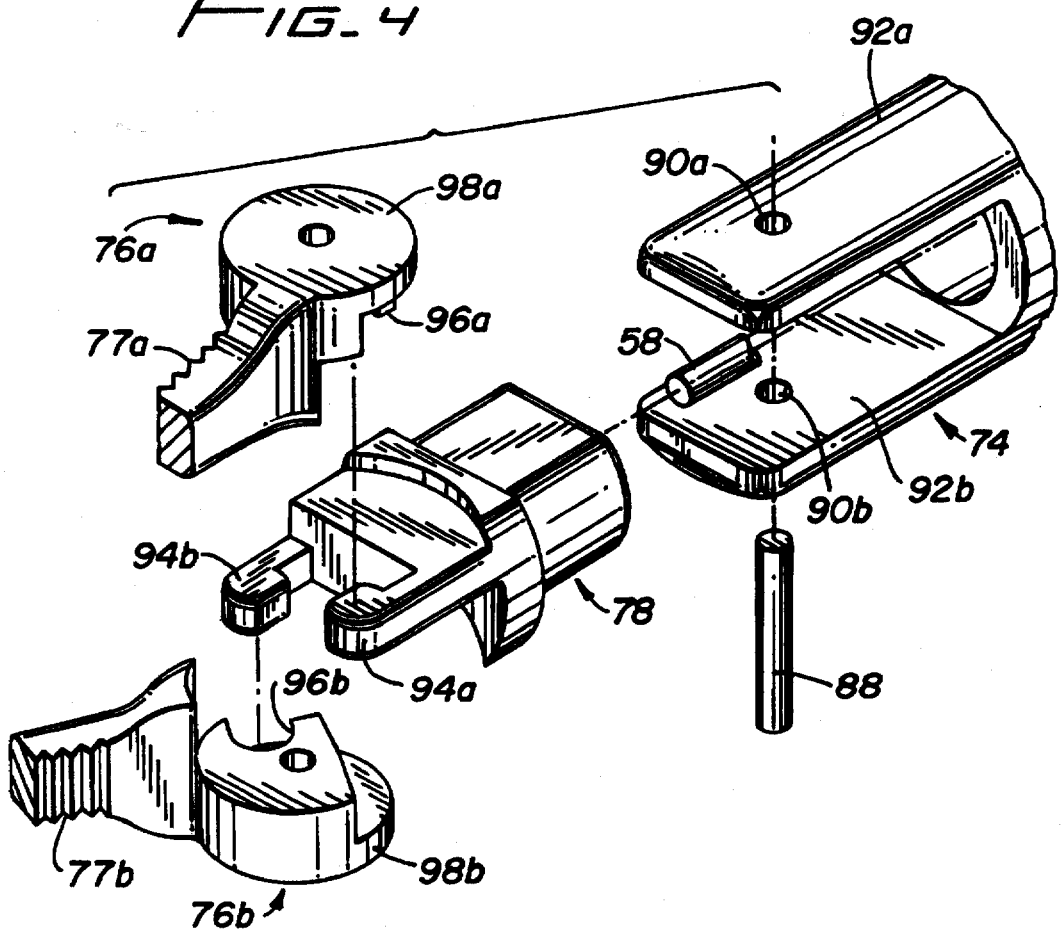

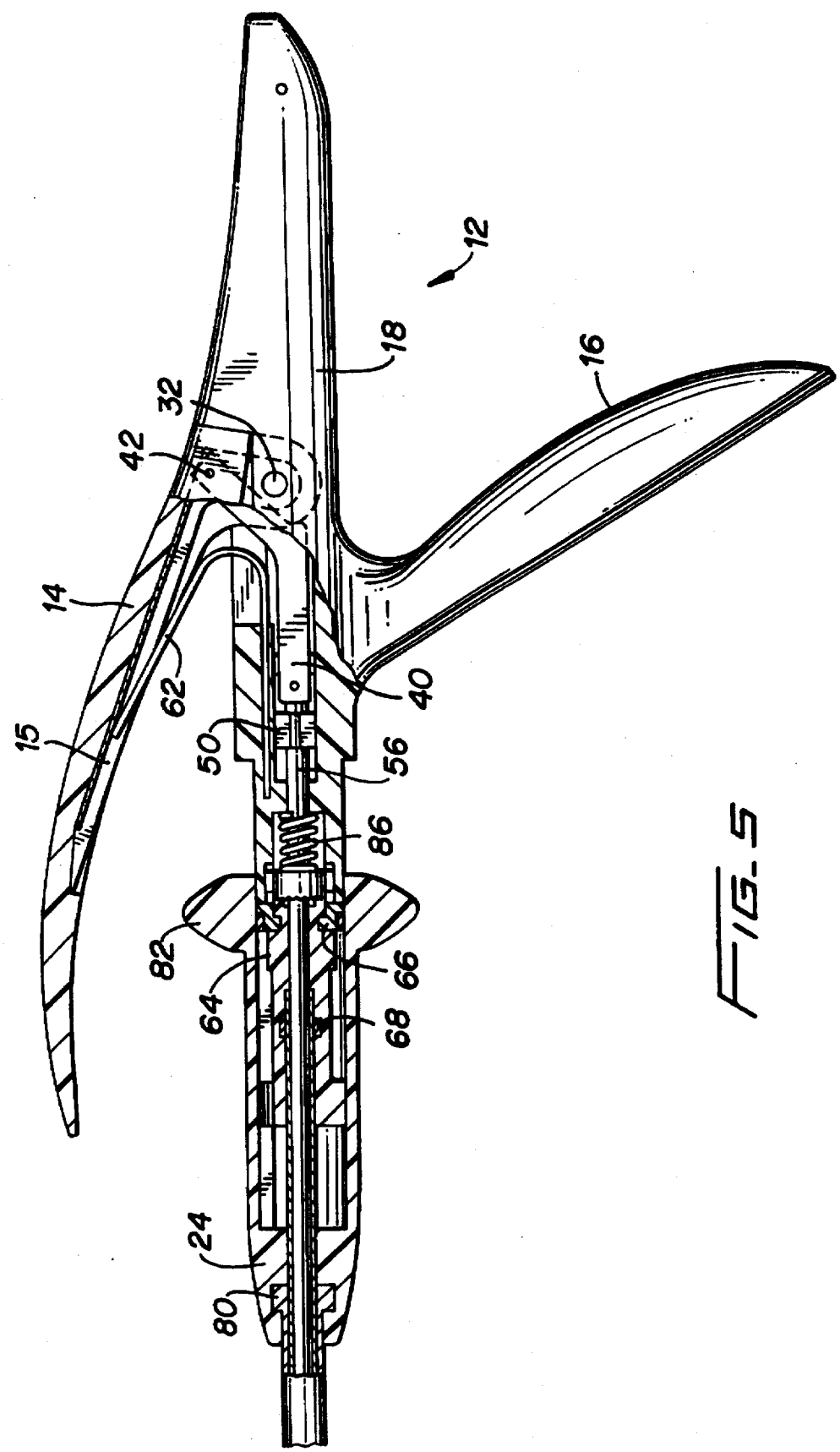

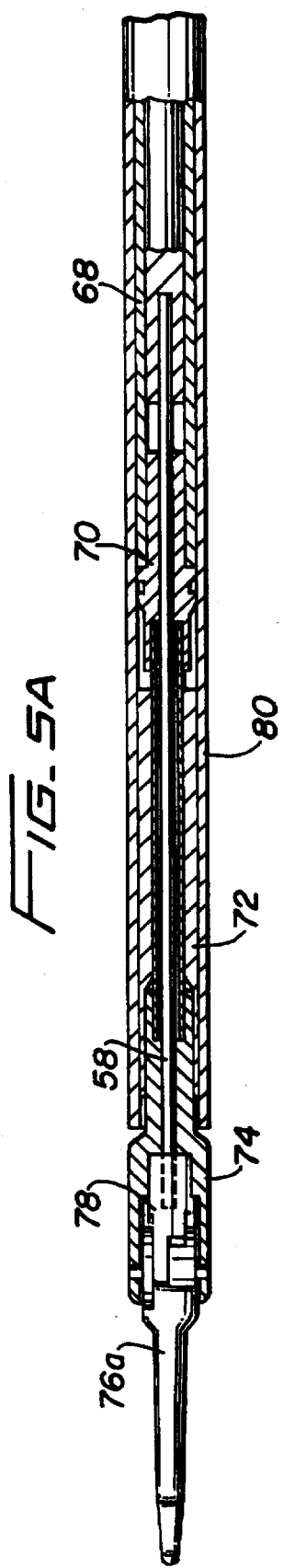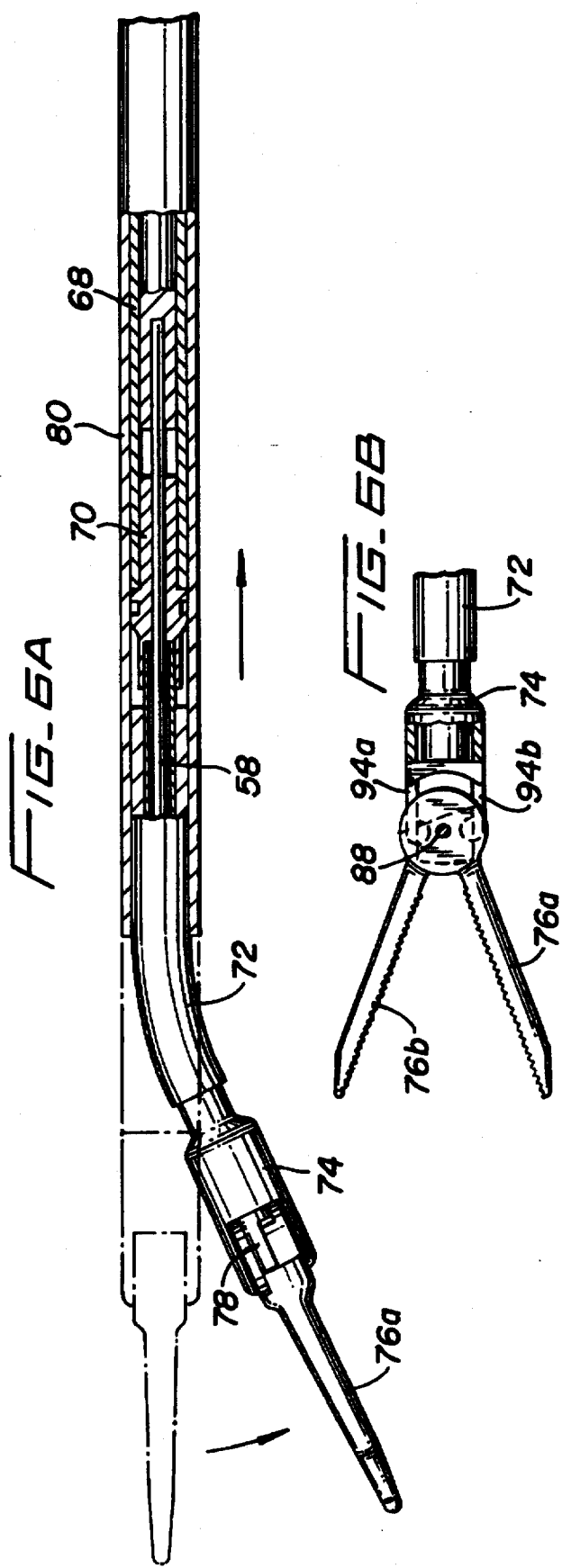

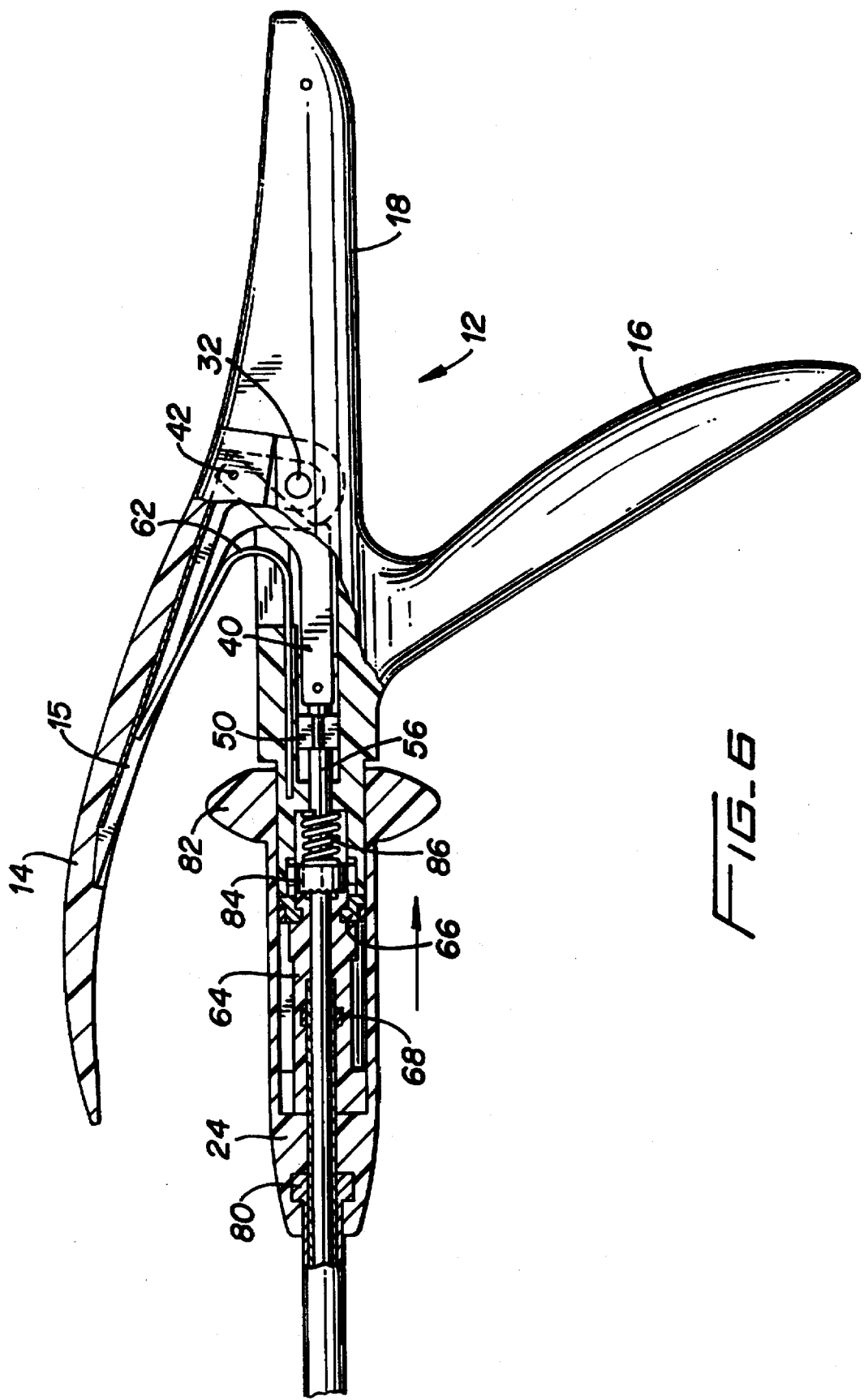

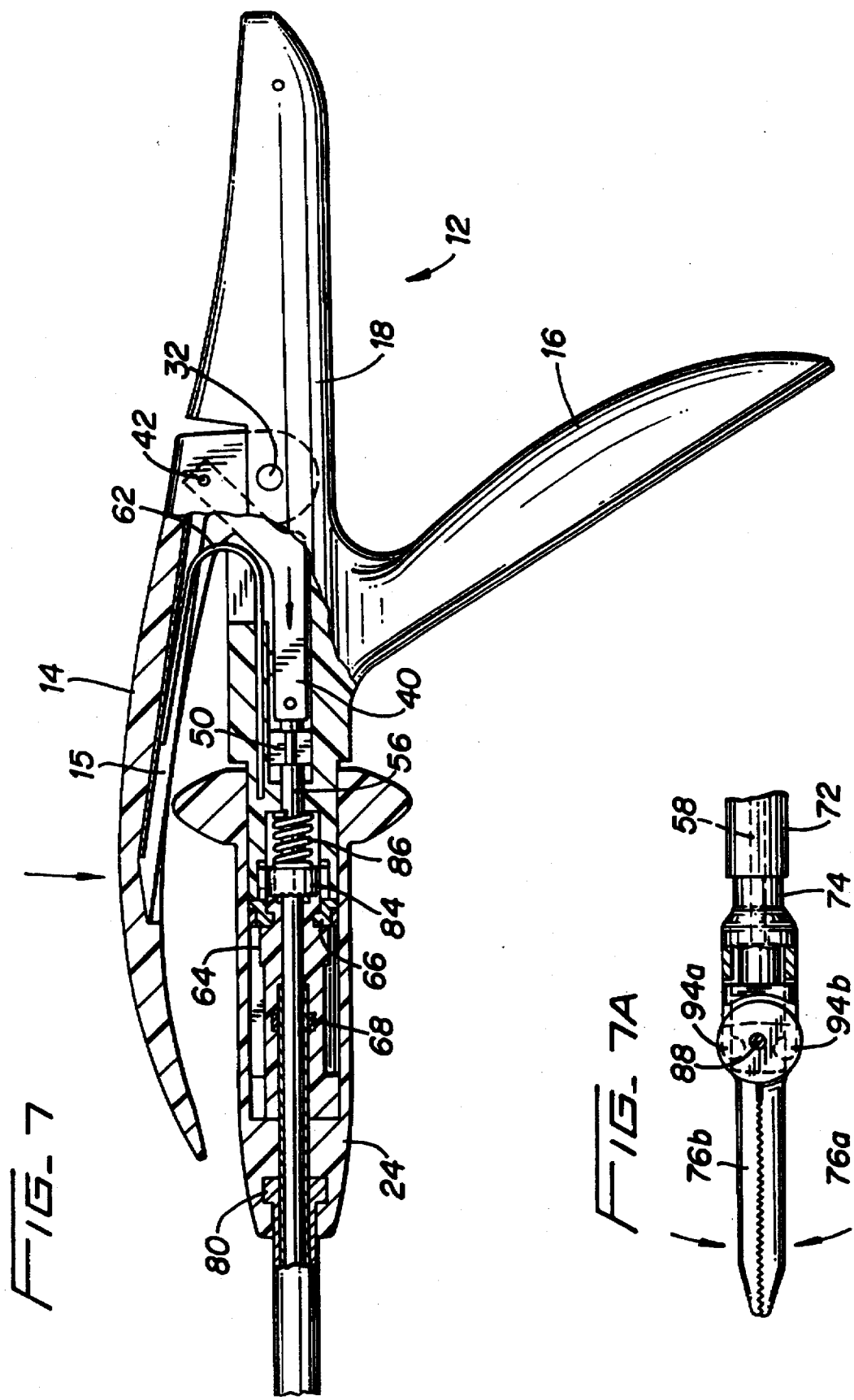

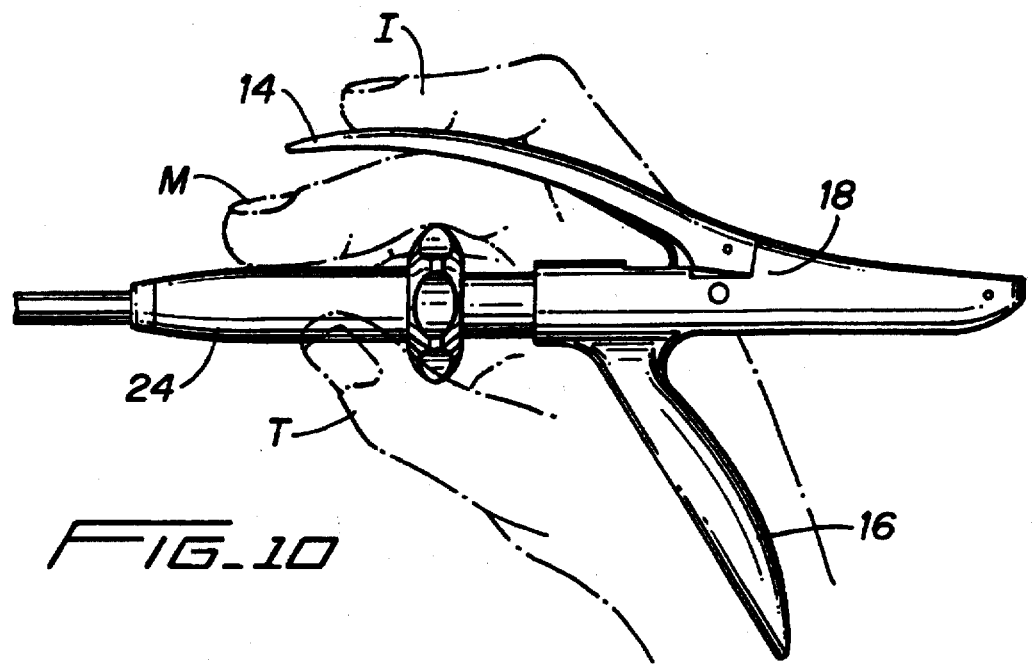
FIG_10
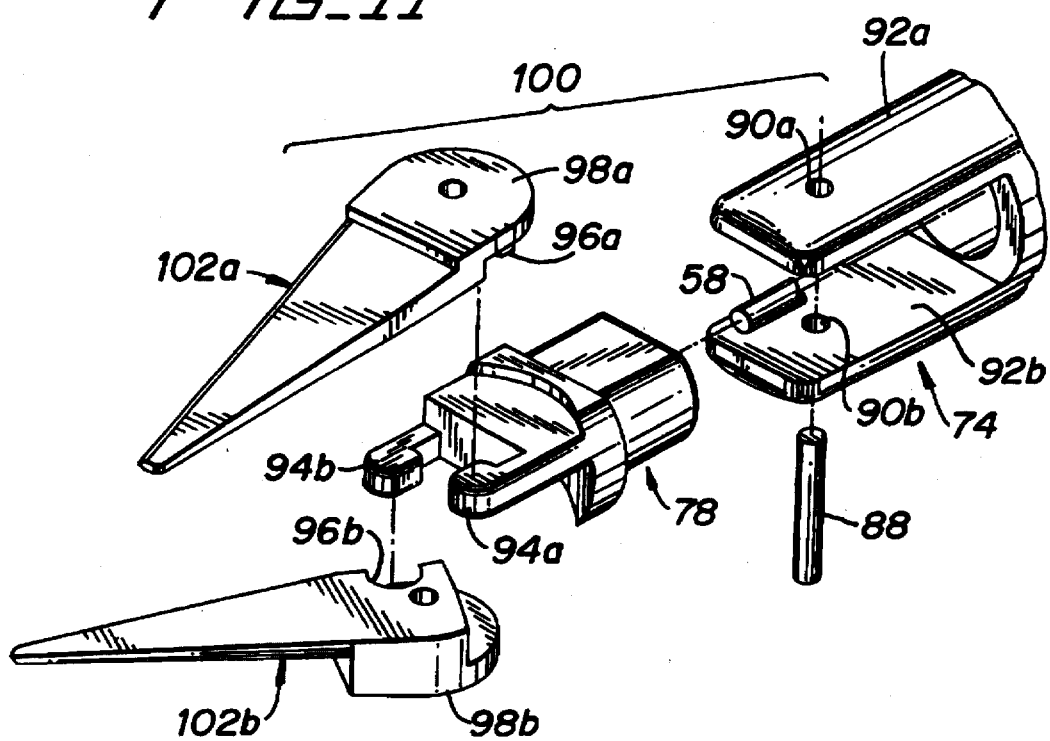
FIG_11

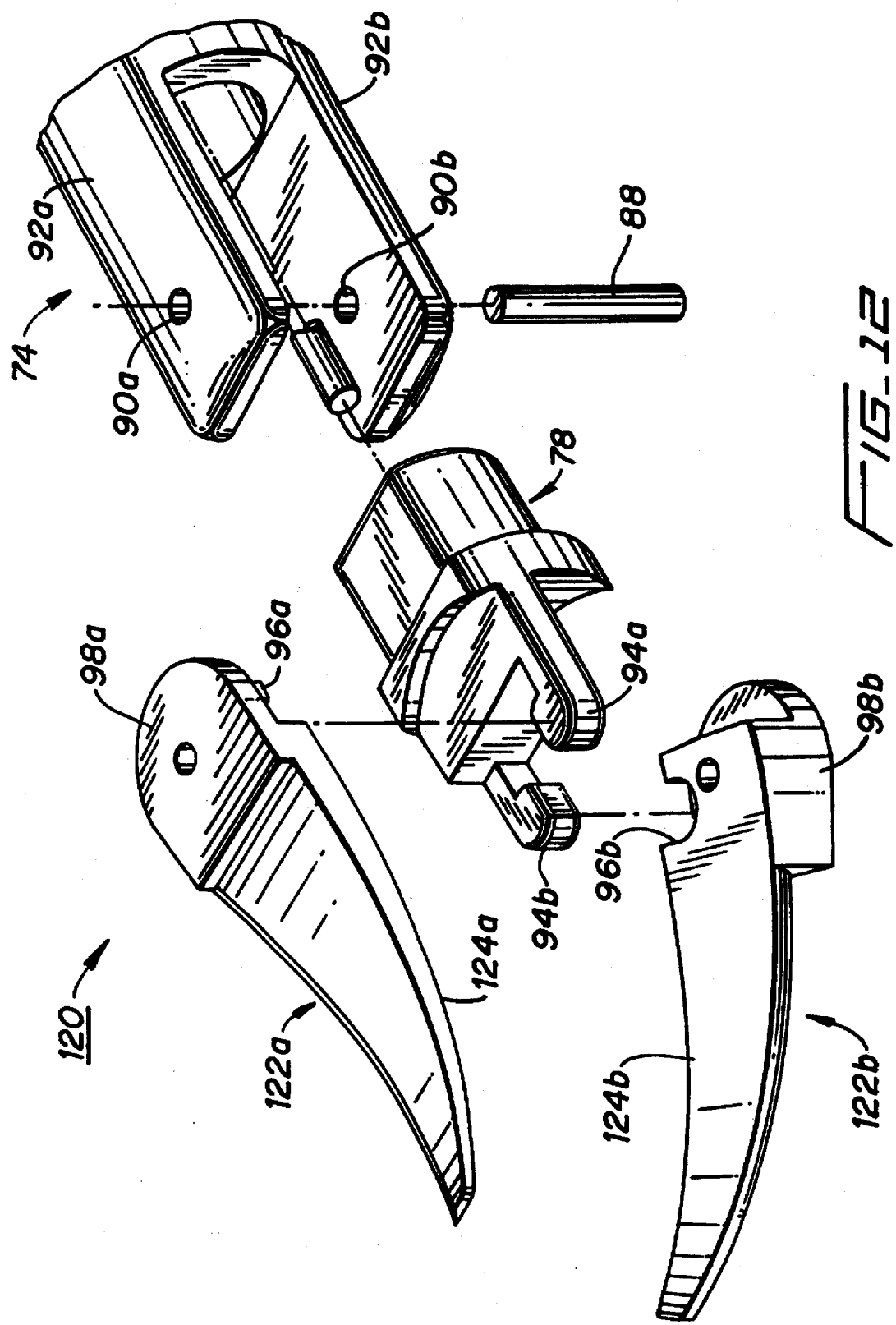

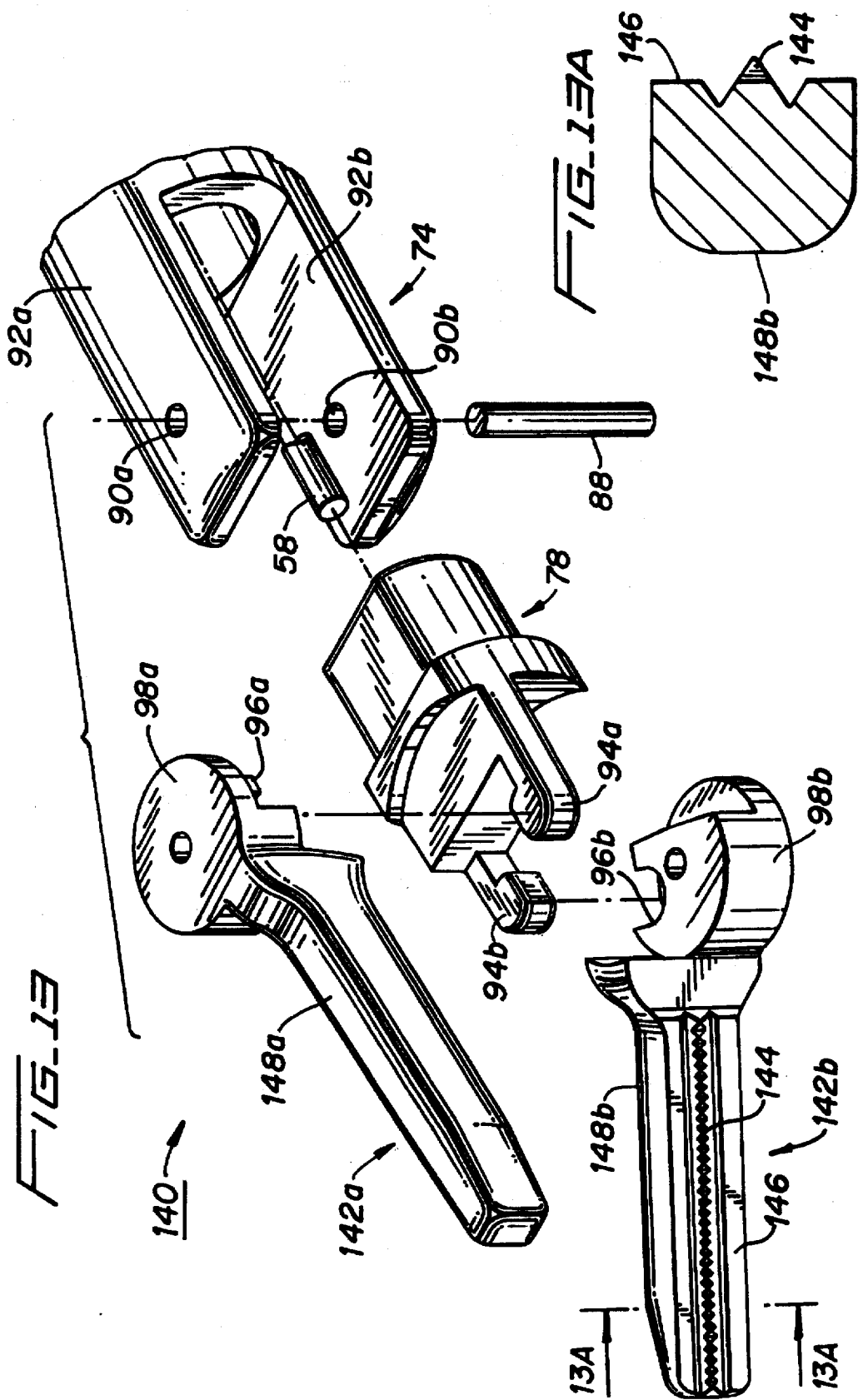

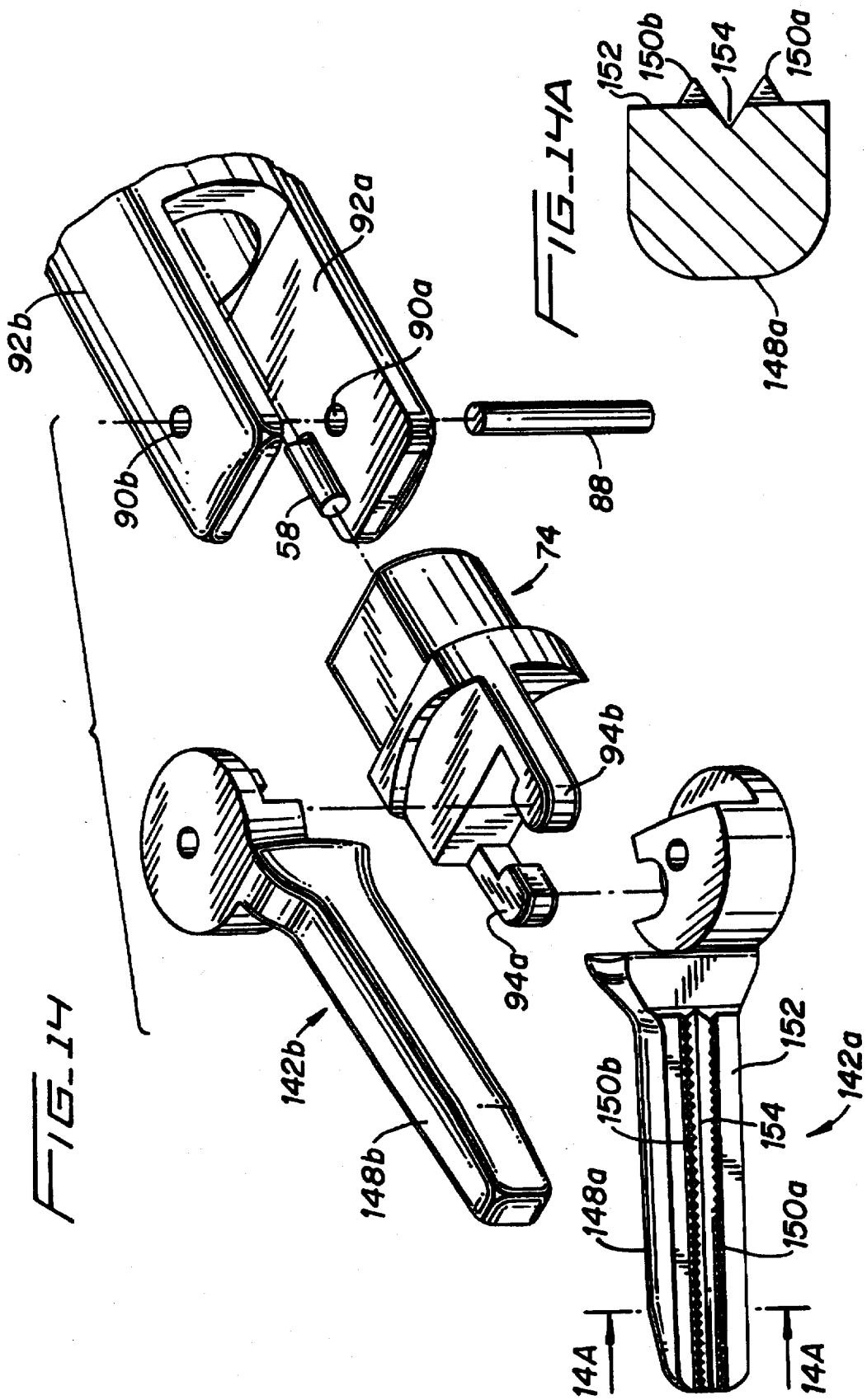

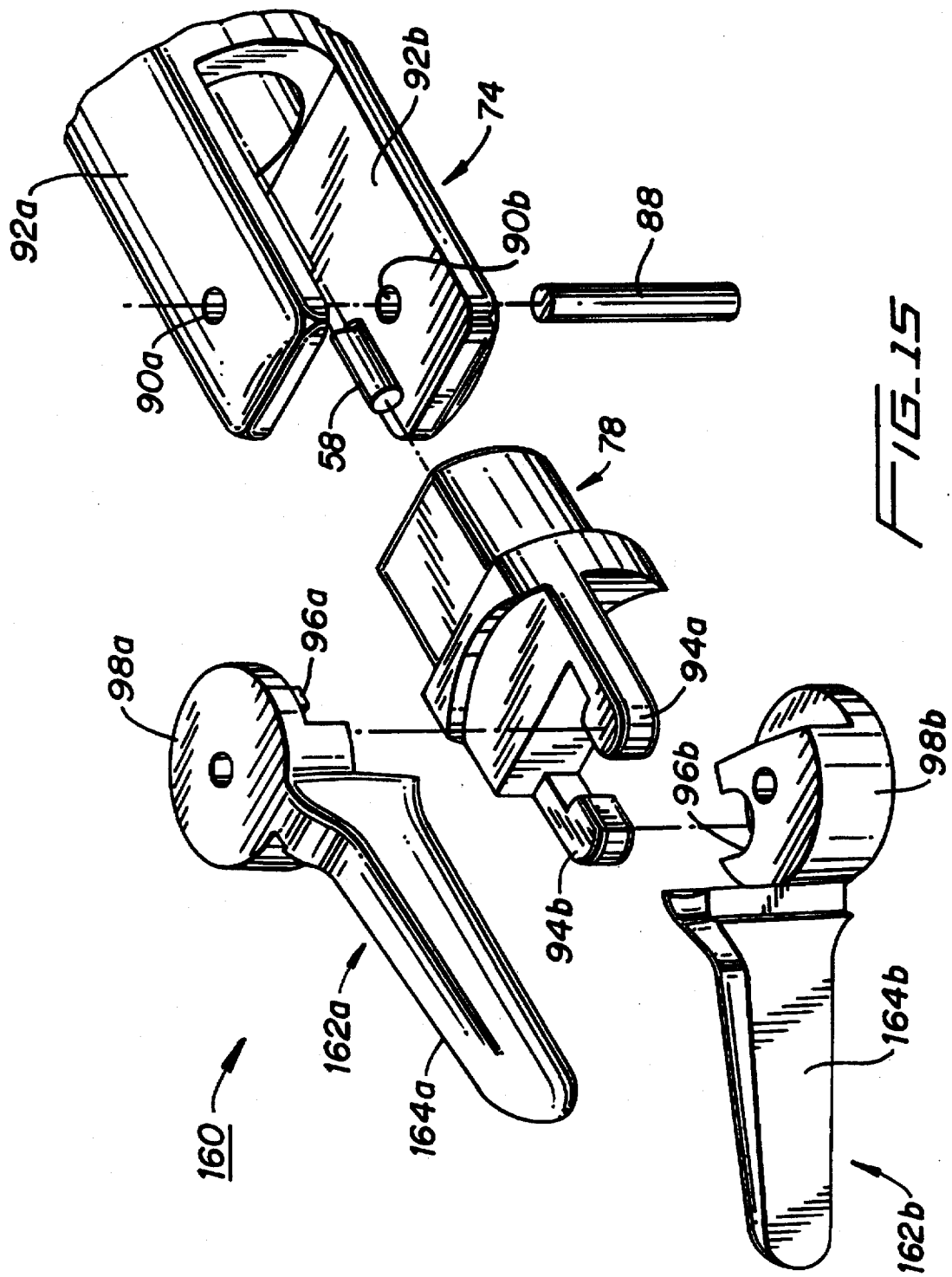

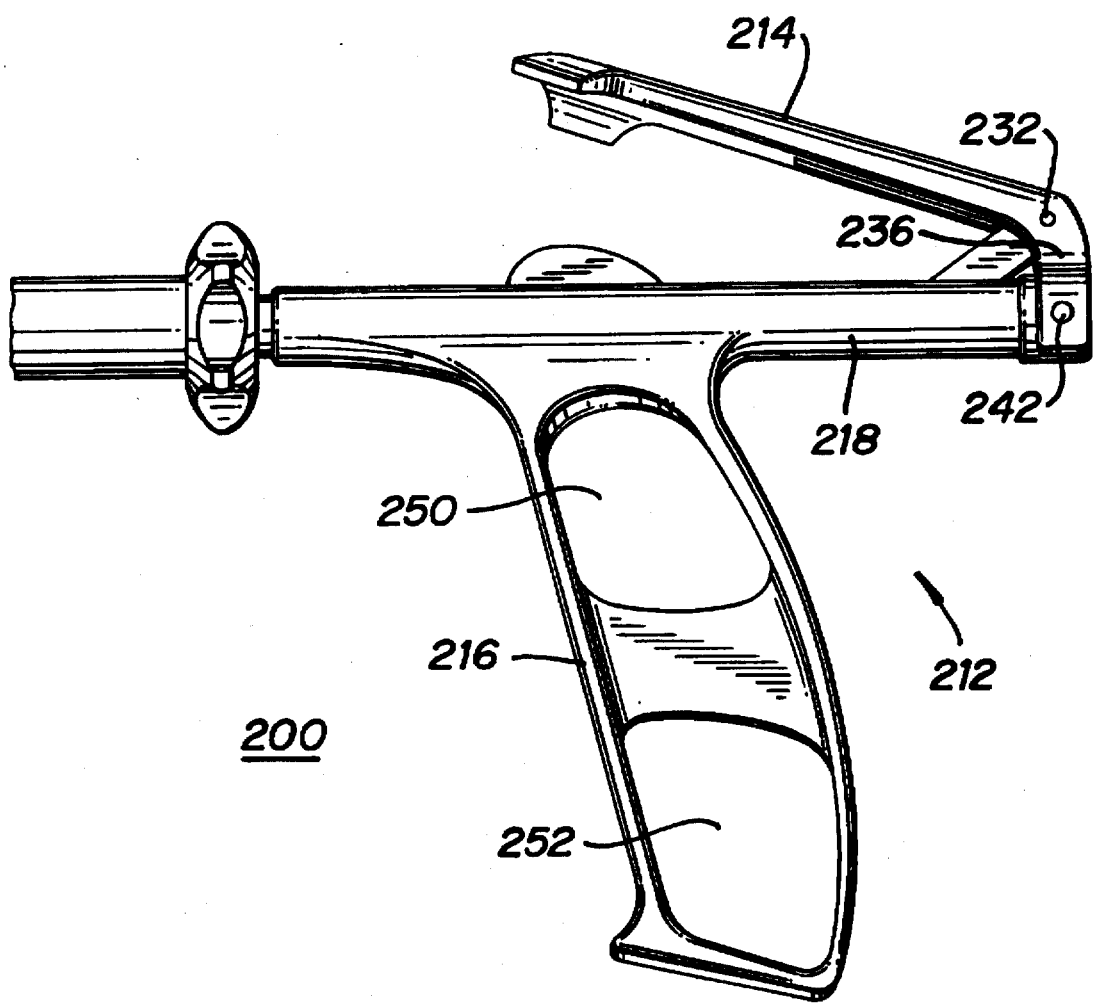

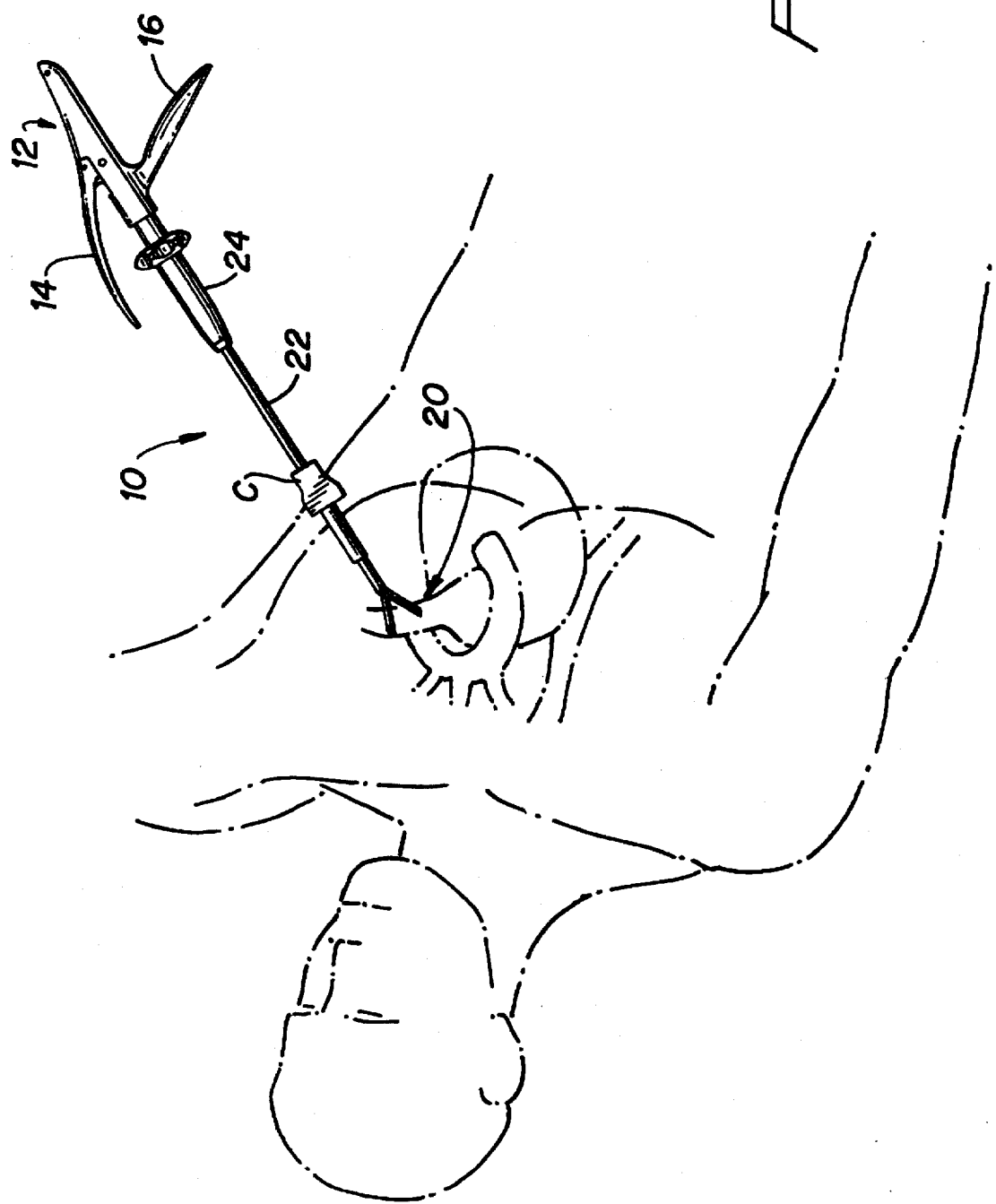

ARTICULATING ENDOSCOPIC SURGICAL INSTRUMENT

BACKGROUND

1. Technical Field

The subject disclosure relates to surgical apparatus for performing minimally invasive surgical procedures through relatively narrow access devices, and more particularly to a handle for a surgical apparatus which is configured to be grasped by the surgeon in a number of different positions.

2. Background of Related Art

In minimally invasive surgical procedures a small incision or puncture is made in the patient's body to provide access for a port or cannula device. The port allows insertion of various surgical instruments such as grasping jaws, scissors, or retractors to perform the surgery. For example, thoracoscopic techniques have been developed for performing surgery on the heart and coronary vessels. Procedures such as coronary artery bypass grafting may be performed under visualization by means of an endoscope.

One advantage of endoscopic and laparoscopic procedures is the reduction of trauma to the patient as a result of accessing internal organs through smaller incisions. However, surgical instruments used during such limited access procedures must provide a wide range of operability at the surgical site in order to perform the required surgical procedures. For example, U.S. Pat. No. 4,763,699 to Jaeger discloses a microsurgery instrument with an adjustable angle of operation for obtaining cervical biopsies.

Similarly, U.S. Pat. No. 4,880,015 to Nierman discloses a surgical device having an increased range of operability. In particular, Nierman discloses a biopsy forceps design for use through a flexible fiberoptic bronchoscope. The biopsy forceps includes a handle connected to a thin elongated flexible shaft with a distal portion thereof hinged to the shaft A gasping tool or biopsy forceps is attached to the distal hinged portion. Control wires extend from the handle to the distal end to the shaft for controlling the angular rotation of the distal portion of the instrument. An articulating surgical apparatus is described in commonly-assigned U.S. Pat. No. 5,403,342 to Tovey et al., the disclosure of which is hereby incorporated by reference. This instrument includes a handle assembly, a tubular body extending from the handle assembly, and a tool assembly associated with a distal end of the tubular body. Remote rotation of the tool assembly is effectuated by a rotation mechanism. Remote articulation of the tool assembly is effectuated by an articulation mechanism. The articulating distal end portion of the tubular body is formed from a shape memory alloy having elastic-like qualities.

During limited access surgical procedures, the surgeon may be required to manipulate delicate tissues or to apply more substantive forces to resistant body organs with the same instrument. In addition, the surgeon may be required to operate upon a particular body structure from several different angles without removing the instrument from the body and repositioning the instrument It is therefore desirable to have an instrument having a handle that is capable of being held by the surgeon in a number of different positions to vary the precision and force with which the instrument is used. An instrument is also needed which enables the surgeon to maintain a stable grip thereon during the performance of a surgical procedure.

SUMMARY

The present disclosure is directed to an instrument having a housing defining a longitudinal axis. A handle is operably connected to the housing and defines a longitudinal axis angularly disposed relative to the longitudinal axis of the housing. A fixed support is attached to the housing and defines a longitudinal axis angularly disposed relative to the longitudinal axis of the housing. The fixed support is radially offset with respect to the handle. A body portion is provided which extends distally from the housing. A tool assembly operatively associated with a distal end portion of the body portion is actuable by the handle. The handle is configured and mounted to be actuated by either the thumb or the fingers of an operator's hand.

In a preferred embodiment, the surgical apparatus includes an actuator for effectuating remote articulation of the tool assembly between a first position substantially parallel to the longitudinal axis of the housing and a second position angularly disposed with respect to the longitudinal axis of the housing. The surgical apparatus may further include a resilient member interconnecting the tool assembly to the distal end portion of the body portion. The resilient member is movable between a first, substantially straight configuration and a second, angular configuration. The actuator includes a tube which coaxially surrounds the body portion and the resilient member and which is mounted for longitudinal movement with respect to the elongated body portion and resilient member. The resilient member is preferably formed of a shape memory alloy.

The present surgical instrument preferably includes a rotation assembly for effectuating remote rotation of the tool assembly about the longitudinal axis of the housing. The rotation assembly includes an axially rotatable collar member rotatably mounted with respect to the housing.

These and other features of the surgical instrument will become more readily apparent to those skilled in the art from the following detailed description of preferred embodiments of the subject disclosure.

BRIEF DESCRIPTION OF THE DRAWINGS

Various embodiments of the subject surgical apparatus are described herein with reference to the drawings wherein:

FIG. 1 is a perspective view of a surgical instrument constructed in accordance with a first embodiment of the subject disclosure;

FIG. 2 is a perspective view with parts separated of the surgical instrument of FIG. 1;

FIG. 3 is an enlarged cross-sectional view of a portion of the handle assembly, taken along line 3—3 of FIG. 1;

FIG. 4 is an enlarged perspective view with parts separated of the jaw assembly of the surgical instrument of FIG. 1 and showing a portion of the jaws;

FIG. 5 is an enlarged side view in partial cross-section of the handle assembly, illustrating the slide barrel disposed in a distal position with respect to the housing;

FIG. 5A is an enlarged side view in partial cross-section of the endoscopic portion of the surgical instrument of FIG. 1;

FIG. 6 is an enlarged side view in partial cross-section of the handle assembly, illustrating the slide barrel disposed in a proximal position with respect to the housing;

FIG. 6A is an enlarged side view in partial cross-section of the endoscopic potion, illustrating the tool assembly in an articulated configuration;

FIG. 6B is an enlarged top view in partial cross-section of the jaw assembly, illustrating the jaws in a spaced apart configuration;

FIG. 7 is an enlarged side view in partial cross-section of the handle assembly, illustrating the pivoting handle in a closed position to close the jaws;

FIG. 7A is an enlarged top view in partial cross-section of the jaw assembly, corresponding to the position of the handle in FIG. 7, illustrating the jaws in a closed configuration;

FIG. 10 is a side view of the handle assembly, illustrating the user's hand positioned in a "tweezer grip" with respect to the handle assembly;

FIG. 11 is an enlarged perspective view with parts separated of the tool assembly of the subject surgical instrument in accordance with another embodiment of subject disclosure;

FIG. 12 is an enlarged perspective view of a tool assembly in accordance with a third embodiment FIG. 13 is an enlarged perspective view with parts separated of a tool assembly in accordance with a fourth embodiment;

FIG. 13A is an enlarged cross-sectional view taken along line 13A—13A of FIG. 13, illustrating a jaw portion having a single row of teeth on an inner surface thereof;

FIG. 14 is an enlarged perspective view with parts separated of the tool assembly of FIG. 13 inverted in viewing angle;

FIG. 14A is an enlarged cross-sectional view taken along line 14A—14A of FIG. 14, illustrating a jaw portion having a double row of teeth on an inner surface thereof;

FIG. 15 is an enlarged perspective view of a tool assembly for grasping a needle in accordance with a fifth embodiment;

FIG. 16 is a side view of a handle assembly constructed in accordance with an alternate embodiment of the subject disclosure; and FIG. 17 is a side view showing insertion of the instrument of FIG. 1. through a cannula.

DETAILED DESCRIPTION OF PREFERRED EMBODIMENTS

Figure 8:
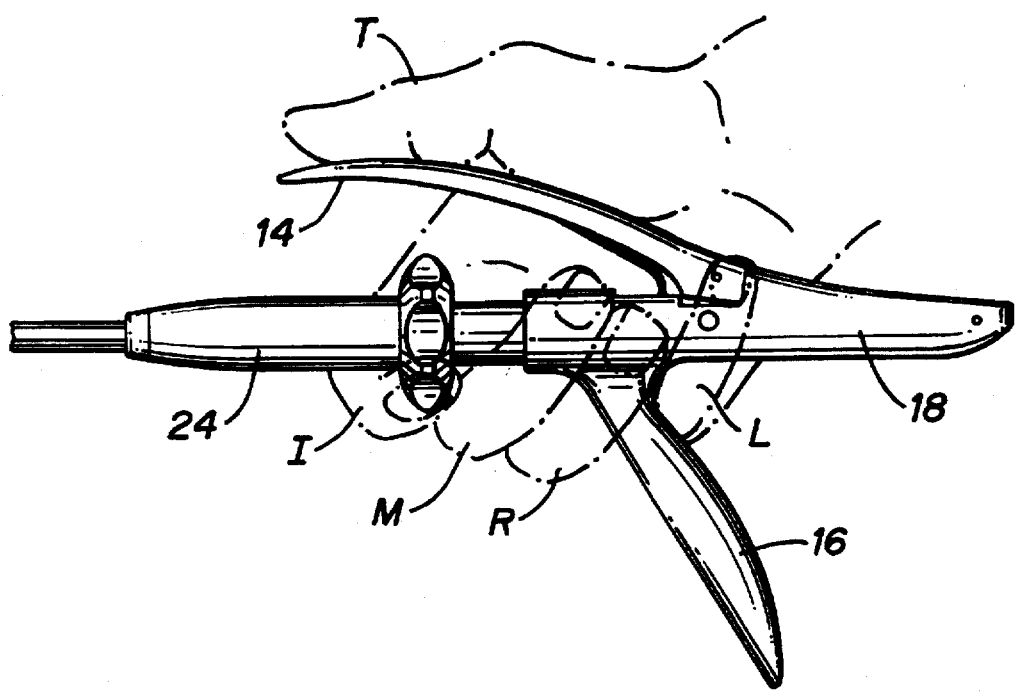
FIG. 8 is a side view of the handle assembly, illustrating the user's hand positioned in a "palm grip" with respect to the handle assembly.

The preferred embodiments of the apparatus disclosed herein will be discussed in terms of minimally-invasive surgical procedures and apparatus. However, use herein of terms such as "thoracoscopic" or "endoscopic" should not be construed to limit the subject disclosure to an apparatus for use in conjunction with a trocar sleeve or an endoscopic tube. The subject apparatus may find use in surgery wherein access to the surgical site is achieved through a narrow cannula or a small incision.

In the drawings and in the description which follows, the term "proximal", as is traditional, will refer to the end of the apparatus which is closer to the operator, while the term "distal" will refer to the end which is further from the operator.

Referring now in detail to the drawings in which like reference numerals identify similar or identical elements, a preferred embodiment of the subject disclosure is illustrated in FIG. 1, and is designated generally by reference numeral 10. Surgical instrument 10 includes handle assembly 12 having movable or pivoting handle 14 and fixed support 16 attached to housing 18. Pivoting handle 14 at least partially extends in a first direction at an angle to a longitudinal axis defined by elongated housing 18. Fixed support 16 at least partially extends in a second direction at an angle to the longitudinal axis of housing 18. Handle 14 and fixed support 16 are radially offset with respect to one another. For example, fixed support 16 and handle 14 may be offset by 180° and be disposed on opposite sides of the housing 18. Other relative positions of fixed support 16 and handle 14 are contemplated. Pivoting handle 14 remotely actuates tool assembly 20 through endoscopic body portion 22. Slide barrel 24 is movably mounted with respect to housing 18 and is configured to articulate tool assembly 20 with respect to the longitudinal axis of endoscopic body portion 22. Slide barrel 24 also facilitates remote angular rotation of tool assembly 20 about the longitudinal axis of housing 18. Body portion 22 and tool assembly 20 are preferably dimensioned to be inserted in a trocar or cannula.

Housing 18 includes left and right housing halves 26a and 26b, respectively (see FIG. 2). Housing halves 26a and 26b are relatively positioned by insertion of pin 28 into aperture 30 of housing half 26b and secured together by sonic welding or other known techniques. Additional stiffening is provided to pivoting handle 14 by reinforcing member 15 which is disposed within a recess in pivoting handle 14. Reinforcing member 15 is fabricated from a rigid material such as steel. Pivoting handle 14 is mounted to housing 18 by pivot pin 32 passing through a pair of pivot apertures 34a in clevis portion 36 of pivoting handle 14, through a pair of apertures 35a in reinforcing member 15, and through corresponding apertures 38a and 38b in housing halves 26a and 26b respectively. This mounting permits pivotal motion of handle 14 with respect to housing 18. Preferably, clevis portion 36 of pivoting handle 14 is disposed entirely within housing 18.

Clevis portion 36 of pivoting handle 14 is connected to a driver member, such as drive link 40, by link pin 42 passing through apertures 44a and 44b in clevis 36 and aperture 46 in drive link 40. Drive link 40 is mounted within longitudinal channel 48 defined in housing halves 26a and 26b for reciprocal longitudinal motion therein. A distal end portion of drive link 40 is connected to rod mounting block 50, which is longitudinally slidable within stepped bore 52 defined in housing halves 26a and 26b and which is in communication with channel 48.

Center rod 56 is mounted at a proximal end portion thereof to rod mounting block 50 and at a distal end portion to cable 58 by connector element 60. Cable 58 actuates tool assembly 20, i.e. opens and closes the jaws of the tool assembly, as will be described in greater detail below. Rod mounting block 50, center rod 56, connector 60 and cable 58 are longitudinal slidable with drive link 40 in response to pivoting movement of pivoting handle 14. A biasing member, such as leaf spring 62, normally biases pivoting handle 14 in a spaced position from housing 18. Consequently, drive link 40 and cable 58 are biased in a proximal direction.

Tool assembly 20 is supported at the distal end portion of surgical instrument 10. Detent shaft 64 is rotatably mounted to housing 18 by annular containing ring 66. Inner tube 68 is coaxially mounted within detent shaft 64. Tube connector 70 joins inner tube 68 and flexible articulating tube 72. A longitudinal bore is defined from detent shaft 64 and through inner tube 68, tube connector 70, and mounting tube 72 to permit center rod 56 and cable 58 to pass coaxially therethrough.

Tool assembly 20 is mounted at a distal end portion of articulating tube 72. In the embodiment of FIG. 2, tool assembly 20 is a jaw assembly for grasping vascular tissue therewith. Other tool assemblies are contemplated and described below. Jaw mounting clevis 74 is connected to articulating tube 72 and supports first and second juxtaposed jaw portions 76a and 76b movable between an approximated (closed) position in which jaw potions 76a and 76b are in relatively close relation to one another and a spaced (open) configuration in which jaw portions 76a and 76b are separated. Jaw portions 76a and 76b are moved by jaw drive link 78 which is connected to cable 58 for reciprocal longitudinal movement therewith. Jaw portions 76a and 76b may be formed with a series of teeth 77a and 77b for grasping tissue therebetween. (see also FIG. 4)

Slide barrel 24 is connected to outer tube 80 and longitudinally slidable therewith with respect to housing 18 and detent shaft 64. Slide barrel 24 is rotatable with detent shaft 64. Outer tube 80 at least partially coaxially surrounds inner tube 68, as will be described below.

Referring now to FIG. 3 in conjunction with FIG. 2, angular rotation of tool assembly 20 is remotely achieved by rotation of fluted portion 82 of slide barrel with respect to housing 18. Rotation is indexed by interaction of detent shaft 64 with floating detent 84 positioned within stepped bore 52. Floating detent 84 is longitudinally slidable in stepped bore 52 but inhibited from angular rotation therein. Floating detent 84 has a radial gearing 83 formed on a distal face thereof which is normally biased into engagement with a corresponding radial gearing 85 on a proximal face of detent shaft 64 by spring 86. Rotation is effected by application of rotational torque by the user, and unrestricted and unintentional rotation is prevented.

Actuation of jaw portions 76a and 76b is accomplished by longitudinal movement of jaw drive link 78 connected to cable 58. Jaw portions 76a and 76b are pivotably mounted to clevis 74 by pivot pin 88 passing through apertures 90a and 90b in spaced apart shackles 92a and 92b as best seen in FIG. 4. Jaw link 78 includes a pair of offset prongs 94a and 94b for respectively engaging peripheral semicircular recesses 96a and 96b in mounting portions 98a and 98b of jaw portions 76a and 76b. In particular, upon distal movement of jaw drive link 78, prongs 94a and 94b ride in recesses 96a and 96b and thereby pivot jaw portions 76a and 76b closed. Proximal motion of jaw drive link 78 pivots jaw portions 76a and 76b to a spaced apart configuration.

FIGS. 5-5A illustrate surgical instrument 10 with tool assembly 20 in a non-articulated configuration and FIGS. 6-6A illustrate tool assembly 20 in an articulated configuration. As illustrated in FIG. 5, slide barrel 24 is disposed in a first, distal position with respect to housing 18. Outer tube 80 is connected to slide barrel 24 and slidable therewith. FIG. 5A illustrates that outer tube 80 is likewise disposed in a first, distal position with respect to articulation tube 72. Outer tube 80 is constructed from a substantially rigid material. However, cable 58 is preferably formed of a resilient shape memory alloy such as Tinel (Nickel Titanium Alloy), the configuration of which can be controlled mechanically by applying a stress to the material. In the present embodiment, the unstressed shape of the cable is an elbow configuration defining an angular configuration with respect to the longitudinal axis of housing 18. The provision of a particular angle will be dictated by the surgical conditions and other angles are contemplated. Articulation tube 72 coaxially surrounds cable 58 and enables it to move between the stressed and the unstressed configurations. When outer tube 80 is disposed in a distal position, cable 58 and articulation tube 72 are surrounded by outer tube 80 and cable 58 is maintained in a substantially straight, unarticulated configuration.

When slide barrel 24 is disposed in a second, proximal position with respect to housing 18 as shown in FIG. 6, tool assembly 20 is articulated. More specifically, outer tube 80 is withdrawn proximally and flexible articulation tube 72 is exposed therefrom. (FIG. 6A) Cable 58 is thereby permitted to return to its unstressed configuration, and tool assembly 20 articulates with respect to the longitudinal axis. Progressive articulation is enabled by selectively moving slide barrel 24 and outer tube 80 between the first distal position and the second, proximal position.

FIG. 6B illustrates juxtaposed jaw portions 76a and 76b in a spaced apart configuration. As described above with respect to FIG. 2, leaf spring 62 normally biases pivoting handle 14 in a spaced configuration from housing 18 and therefore normally biases cable 58 and jaw link 78 in a proximal position by operative connection to drive link 40. When jaw link 78 is disposed in a proximal position, jaw portions 76a and 76b are in a spaced apart configuration as shown in FIG. 6B. Consequently, the normally spaced position of pivoting handle 14 from housing 18 as shown in FIGS. 5 and 6 corresponds with the spaced apart configuration of jaw portions 76a and 76b.

Approximation of juxtaposed jaw portions 76a and 76b is effected by closure of pivoting handle 14 towards housing 18. FIG. 7 illustrates pivoting handle 14 approximated with housing 18 against the normal bias of leaf spring 62. Link pin 42, which is offset from pivot pin 32 conveys drive link 40 distally within channel 48. Consequently, rod mounting block 50 and center rod 56 move distally. Cable 58 (illustrated in phantom) operatively connected to center rod 56 moves jaw drive link 78 distally to close jaw portions 76a and 76b (FIG. 7A) by camming interaction of prongs 94a and 94b with recesses 96a and 96b of jaw portions 76a and 76b respectively.

Figure 9:
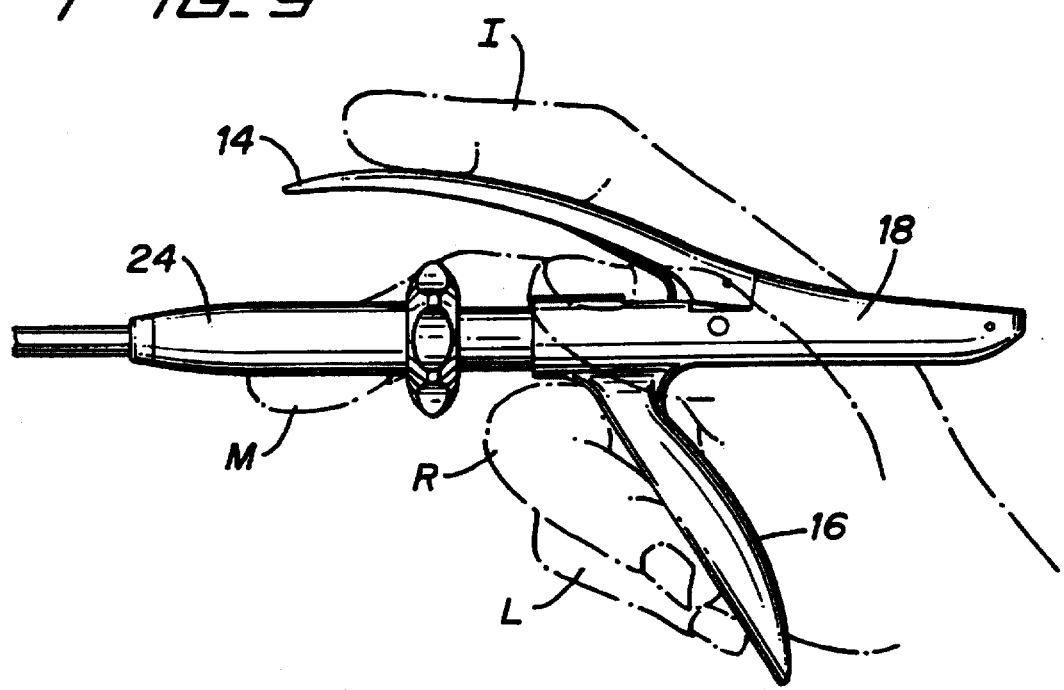
FIG. 9 is a side view of the handle assembly, illustrating the user's hand positioned in a "pistol grip" with respect to the handle assembly.

Turning now to FIGS. 8-10, surgical instrument 10 may be grasped by the user in several different positions as dictated by surgical conditions and to permit precise operation in limited access procedures. In FIG. 8, surgical instrument 10 is held by the user in a "palm grip" with index finger I, middle finger M, ring finger R, and little finger L positioned surrounding housing 18. Thumb T rests on pivoting handle 14. Palm grip permits the user to make use of the greater leverage of thumb T on pivoting handle 14 in situations requiring significant closing force by jaw portions 76a and 76b.

In FIG. 9, surgical instrument 10 is held by the user in a "pistol grip". Housing 18 is gripped between thumb T and middle finger M, and further stability is provided by ring finger R and little finger L resting on fixed support 16. Pistol grip provides more precision than palm grip (FIG. 8) but closing force provided by index finger I on pivoting handle 14 is reduced somewhat in comparison to the closing force provided by thumb T.

In FIG. 10, surgical instrument 10 is held in a "tweezer grip" by the user. Surgical instrument 10 is grasped at slide barrel 24 between thumb T and middle finger M. Pivoting handle 14 is actuated by the distal extremity of index finger I. Tweezer grip provides the user with the greatest precision in performing delicate surgical procedures.

A second embodiment of the tool assembly, designated by reference numeral 100 is illustrated in FIG. 11 and operates substantially as described above with respect to tool assembly 20, with the differences noted below. In particular, tool assembly 100 includes a pair of pivoting blades 102a and 102b, which together shear or cut tissue. Blades 102a and 102b have mounting portions 98a and 98b which are pivotably mounted to clevis 74 by pivot pin 88 passing through apertures 90a and 90b in spaced apart shackles 92a and 92b respectively. Jaw link 78 includes a pair of offset prongs 94a and 94b for respectively engaging peripheral semicircular recesses 96a and 96b in mounting portions 98a and 98b of blades 102a and 102b.

A third embodiment of the tool assembly of subject surgical instrument is shown in FIG. 12. Tool assembly 120 operates substantially as described above with respect to tool assembly 100, with the differences noted below. In particular, tool assembly 120 includes a pair of pivoting blades 122a and 122b, which are pivotably mounted to clevis 74 and shear or cut tissue. Blades 122a and 122b include distal body portions 124a and 124b which are curved in an upward direction. The curvature of the blades improves the surgeon's line of sight in cutting tissue.

FIGS. 13–14A illustrate a fourth embodiment of the tool assembly of the subject surgical instrument. Tool assembly 140 includes a pair of pivoting jaw portions 142a and 142b which are pivotably mounted to clevis 74 and operate substantially as described above with respect to tool assembly 20. Jaw portion 142b includes a single row of interdigitating teeth 144 disposed along an inner surface 146 of body portion 148b. Jaw portion 142a has a double row of interdigitating teeth 150a and 150b disposed along an inner surface 152 of body portion 148a. A notch 154 extends between the rows of teeth 150a and 150b for reception of single row of teeth 144 on jaw potion 142b when jaw potions 142a and 142b are approximated. The interlocking configuration of teeth 144 and 150 facilitates the grasping of tissue therebetween and is particularly useful in occluding vascular tissue, ducts or other tubular structures.

A fifth embodiment of the tool assembly is shown in FIG. 15. Tool assembly 160 operates substantially as described above with respect to tool assembly 20, with the differences noted below. Tool assembly 160 includes a pair of pivoting jaw portions 162a and 162b configured to grasp a needle. Jaw portions 162a and 162b are pivotably mounted to clevis 74 and have inner surfaces 164a and 164b configured to grasp a needle or other object therebetween when jaw potions 162a and 162b are approximated.

An alternate embodiment of the handle assembly is shown in FIG. 16 and designated generally by reference numeral 200. Surgical instrument 200 operates substantially as described with regard to surgical instrument 100 above, with the following differences noted below. In particular, handle assembly 212 includes housing 218 defining a longitudinal axis, pivoting handle 214, and fixed support 216. Pivoting handle 214 is pivotably mounted to housing 218 by pivot pin 232 passing through clevis portion 236 of pivoting handle 214. Pivoting handle 214 is angularly disposed relative to the longitudinal axis of housing 218. Fixed support 216 is also angularly disposed relative to the longitudinal axis of housing 218. Pivoting handle 214 and fixed support 216 are radially offset with respect to one another.

Link pin 242 is connected to center rod (not shown) by a well known universal joint assembly (not shown). Center rod is supported within housing 218 for reciprocal longitudinal movement substantially as described for center rod 56 above.

Surgical instrument 200 is configured to be held by the user in the "palm grip", the "pistol grip", and the "tweezer grip" described above. Fixed support 216 depends from housing 218 and defines a first opening 250, and a second opening 252. Surgical instrument 200 may be held in the palm grip by grasping housing 218 with index finger, middle finger, ring finger, and little finger, and by actuating pivoting handle 214 with the thumb. At least one of the index finger and middle finger may be inserted through first opening 250 for additional stability.

Surgical instrument 200 may be held in the pistol grip by passing the middle finger, ring finger, and little finger through first opening 250 and second opening 252, and by resting the thumb against housing 218. The index finger is used to actuate pivoting handle 214. To hold surgical instrument 200 in the tweezer grip, housing 218 is grasped between the thumb and middle finger, and pivoting handle 214 is actuated by the distal extremity of the index finger. It is contemplated that surgical instrument may be grasped in other positions as well.

The above described instruments may have particular use for example in minimally invasive coronary artery bypass procedures to perform particular tasks such as grasping, cutting etc. As shown in FIG. 17, instrument 10 is inserted through cannula C placed between the ribs. It should be noted that use of the aforedescribed instruments in other procedures is also contemplated.

It will be understood that various modifications may be made to the embodiments disclosed herein. For example, different tool assemblies may be used in conjunction with the surgical instrument disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical apparatus, which comprises:
   a) a housing defining a longitudinal axis;
   b) a handle having a first configuration and operably connected to the housing, the handle defining a longitudinal axis angularly disposed relative to the longitudinal axis of the housing;
   c) a fixed support having a second configuration substantially different from the first configuration and depending from the housing, the fixed support defining a longitudinal axis angularly disposed relative to the longitudinal axis of the housing, the support extending from the housing at a position rotated about the longitudinal axis of the housing with respect to the handle;
   d) a body portion extending distally from the housing; and
   e) a tool assembly operably associated with a distal end portion of the body portion and remotely actuable by the handle.

2. A surgical apparatus as recited in claim 1, wherein the handle is configured and mounted to be actuated by an index finger of an operator's hand.

3. A surgical apparatus as recited in claim 2, which further comprises an actuator for effectuating remote articulation of the tool assembly between a first position substantially parallel to the longitudinal axis of the housing and a second position angularly disposed with respect to the longitudinal axis of the housing.

4. A surgical apparatus as recited in claim 3, which further comprises a resilient member interconnecting the tool assembly to the distal end portion of the elongated body portion, the resilient member movable between a first, substantially straight configuration and a second, angular configuration.

5. A surgical apparatus as recited in claim 4, wherein the actuator includes a tube coaxially surrounding the elongated body portion and the resilient member, and mounted for longitudinal movement with respect thereto.

6. A surgical apparatus as recited in claim 4, wherein the resilient member is formed of a shape memory alloy.

7. A surgical apparatus as recited in claim 1, which further comprises:

a rotation assembly for effectuating remote rotation of the tool assembly about the longitudinal axis of the housing.

8. A surgical apparatus as recited in claim 7, wherein the rotation assembly includes an axially rotatable collar member rotatably mounted with respect to the housing.

9. A surgical apparatus as recited in claim 1, wherein the tool assembly is a jaw assembly.

10. A surgical apparatus as recited in claim 1, wherein the tool assembly includes a pair of cutting blades.

11. A surgical apparatus as recited in claim 10, wherein the cutting blades have cutting surfaces with a curvilinear profile.

12. A surgical apparatus as recited in claim 1 further comprising:

an actuator for effectuating remote articulation of the tool assembly between a first position substantially parallel to the longitudinal axis of the housing and a second position angularly disposed with respect to the longitudinal axis of the housing.

13. A surgical apparatus as recited in claim 12, which further comprises a resilient member interconnecting the tool assembly to the distal end portion of the elongated body portion, the resilient member movable between a first, substantially straight configuration and a second, angular configuration.

14. A surgical apparatus as recited in claim 13, wherein the actuator includes a tube coaxially surrounding the elongated body portion and the resilient member, and mounted for longitudinal movement with respect thereto.

15. A surgical apparatus as recited in claim 13, wherein the resilient member is formed of a shape memory alloy.

16. A surgical apparatus as recited in claim 12, which further comprises:

a rotation assembly for effectuating remote rotation of the tool assembly about the longitudinal axis of the housing.

17. A surgical apparatus as recited in claim 16, wherein the rotation assembly includes an axially rotatable collar member rotatably mounted with respect to the housing.

18. A surgical apparatus as recited in claim 1, wherein the handle is pivotably connected to the housing.

19. A surgical apparatus as recited in claim 18, which further comprises a resilient member interconnecting the tool assembly to the distal end portion of the body portion, the resilient member movable between a first, unstressed configuration and a second, stressed configuration.

20. A surgical apparatus as recited in claim 19, wherein the actuator includes a tube coaxially surrounding the body portion and the resilient member, and mounted for longitudinal movement with respect thereto.

21. A surgical apparatus, which comprises:

a) a housing defining a longitudinal axis;

b) a handle lying in a first plane and operably connected to the housing, the handle defining a longitudinal axis angularly disposed relative to the longitudinal axis of the housing, the handle connected at its proximal end to the housing and extending generally distally therefrom;

c) a generally elongated fixed support attached to the housing and lying outside of the first plane, the fixed support defining a longitudinal axis angularly disposed relative to the longitudinal axis of the housing, the support extending from the housing at a position rotated about the longitudinal axis of the housing with respect to the handle;

d) a body portion extending distally from the housing; and e) a tool assembly operably associated with a distal end portion of the body portion and remotely actuable by the handle.

22. A surgical apparatus as recited in claim 21, wherein the handle and the fixed support are configured to be held in a pistol grip fashion.

23. A surgical apparatus as recited in claim 21, wherein the handle and the fixed support are configured to be held in palm grip fashion.

24. A surgical apparatus as recited in claim 21, wherein the handle and the fixed support are configured to be held in tweezer grip fashion.

25. A surgical apparatus as recited in claim 21, wherein the handle and the fixed support are configured to be held in at least two of pistol grip, palm grip and tweezer grip fashion.

26. A surgical apparatus as recited in claim 21, wherein the handle and the fixed support are of approximately the same length.

27. A surgical apparatus, which comprises:

a) a housing defining a longitudinal axis;

b) a handle operably connected to the housing and defining a longitudinal axis angularly disposed relative to the longitudinal axis of the housing;

c) a generally elongated fixed support depending from the housing sufficiently to be grasped by at least two fingers of an operator, the support extending from the housing at a position longitudinally offset along the axis of the housing relative to the handle and defining a longitudinal axis angularly disposed relative to the longitudinal axis of the housing, the support extending from the housing at a position rotated about the longitudinal axis of the housing with respect to the handle;

d) a body portion extending distally from the housing; and e) a tool assembly operably associated with a distal end portion of the body portion and remotely actuable by the handle.

28. A surgical apparatus, which comprises:

a) a housing defining a longitudinal axis;

b) a handle operably connected to the housing and defining a longitudinal axis angularly disposed relative to the longitudinal axis of the housing;

c) a generally elongated fixed support depending from the housing and defining a longitudinal axis angularly disposed relative to the longitudinal axis of the housing, the support extending from the housing at a position rotated about the longitudinal axis of the housing with respect to the handle;

d) a body portion extending distally from the housing; and e) a tool assembly operably associated with a distal end portion of the body portion and remotely actuable by the handle, wherein a first one of the handle and the fixed support extends from the housing in a generally distal direction and a second one of the handle and the fixed support extends from the housing in a direction generally proximal to that of the first one.

29. A surgical apparatus as recited in claim 28, wherein the handle and the fixed support lie in the same plane.

* * * * *